United States Patent [19]

Petiard et al.

[11] Patent Number: 5,030,573
[45] Date of Patent: Jul. 9, 1991

[54] PROCESS FOR CULTIVATING PLANT CELLS IN VITRO

[75] Inventors: Vincent Petiard; Daniel Yvernel, both of Tours, France

[73] Assignee: Nestec S.A., Vevey, Switzerland

[21] Appl. No.: 6,307

[22] Filed: Jan. 15, 1987

Related U.S. Application Data

[63] Continuation of Ser. No. 477,796, Mar. 22, 1983, abandoned, which is a continuation of Ser. No. 313,621, Oct. 21, 1981, abandoned.

[30] Foreign Application Priority Data

Oct. 22, 1980 [FR] France .................. 80 22538

[51] Int. Cl.$^5$ .................. C12N 5/02; C12M 3/02; C12M 1/12
[52] U.S. Cl. .................. 435/240.46; 435/286; 435/311; 435/813
[58] Field of Search .............. 435/240, 241, 813, 946, 435/285, 286, 240.46, 311; 47/1.4

[56] References Cited

U.S. PATENT DOCUMENTS

| | | | |
|---|---|---|---|
| 2,975,553 | 3/1961 | Paul ........................................ | 47/1.4 |
| 3,705,841 | 12/1972 | Lumb et al. ........................ | 435/813 |
| 3,743,582 | 7/1973 | Kitai et al. ......................... | 435/813 |
| 4,115,949 | 9/1978 | Avron et al. ........................ | 47/1.4 |
| 4,220,725 | 9/1980 | Knazek et al. ...................... | 435/240 |
| 4,225,671 | 10/1980 | Puchinger et al. ................. | 435/813 |

OTHER PUBLICATIONS

"Apparatus for the Prolonged Sterile Culture in Vitro of Whole Ropp, Plants or Excised Plant Tissues", Science, 104 (1946), pp. 371–373.

Brodelius et al, "Immobilized Plant Cells for the Production and Transformation of Natural Products", FEBS Letters, 103(1) (1979), pp. 93–97.

Fowler, "Growth of Cell Cultures Under Chemostat Conditions" in, Plant Tissue Culture and Its Bio-Technical Application (1977), pp. 254–259.

Kurz et al, "Plant Cell Cultures, A Potential Source of Pharmaceuticals", Advances In Applied Microbiology, vol. 25 (1979), pp. 212–225 and 229.

Butcher, "Secondary Products in Tissue Cultures" in, Applied and Fundamental Aspects of Plant Cell, Tissue, and Organ Culture, pp. 690–693.

Abbott, "Immobilized Cells" in, Annual Reports on Fermentation Processes, vol. 2 (1978), pp. 96–101.

Kurz, "A Chemostat for Single Cell Cultures of Higher Plants" in, Tissue Culture Methods and Applications (1973), pp. 359–363.

Primary Examiner—Jacqueline Stone
Assistant Examiner—Davis T. Fox
Attorney, Agent, or Firm—Wegner, Cantor, Mueller & Player

[57] ABSTRACT

Plant cells are cultivated in vitro without agitation or fixation, e.g. for the production of a metabolite or a biotransformation. The liquid medium may be circulated for removal of the desired products.

8 Claims, 1 Drawing Sheet

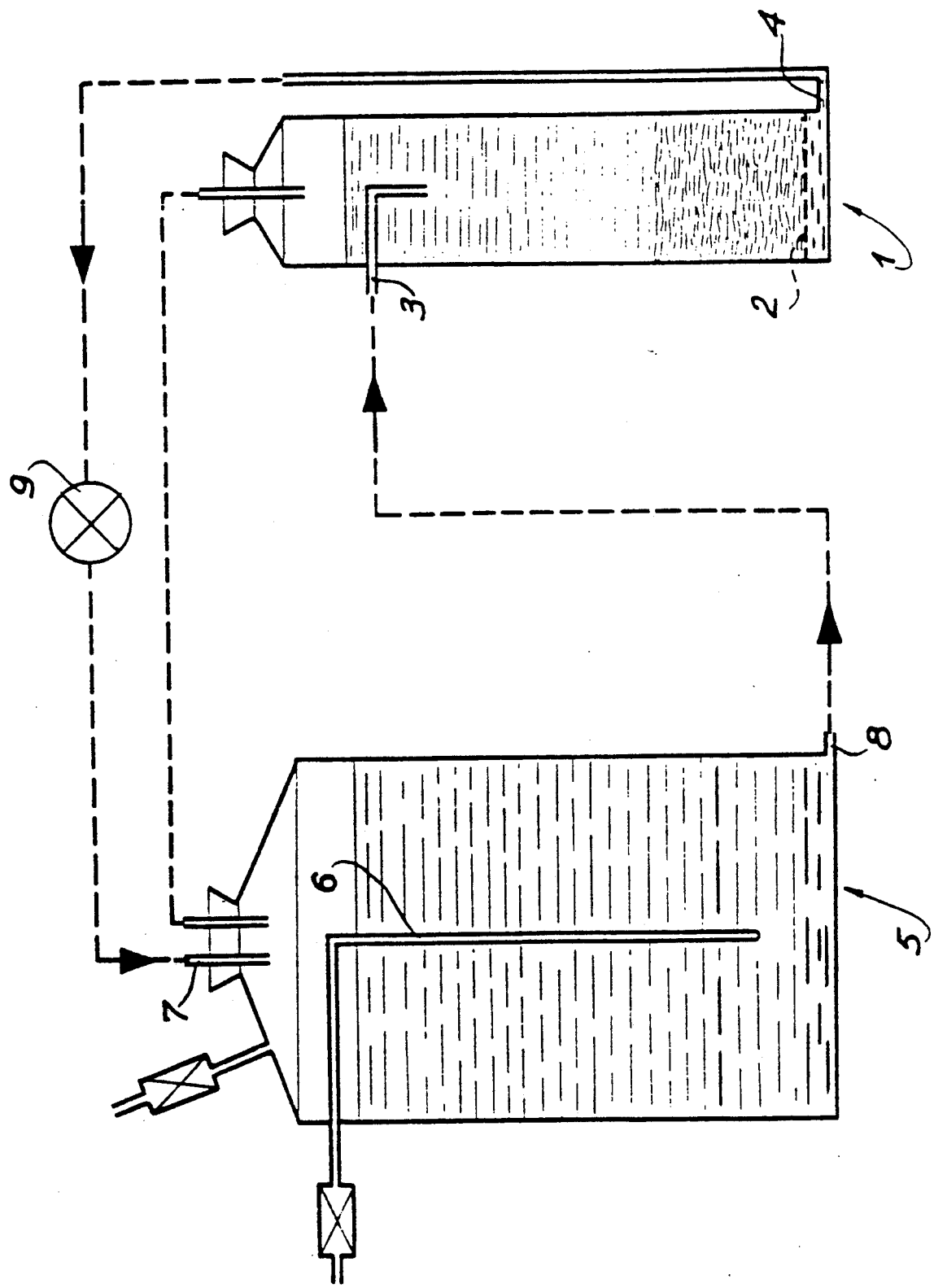

PROCESS FOR CULTIVATING PLANT CELLS IN VITRO

This application is a continuation of U.S. application Ser. No. 477,796, filed Mar. 22, 1983, which is a continuation of U.S. application Ser. No. 313,621, filed Oct. 21, 1981.

DESCRIPTION

The present invention relates to the cultivation of plant cells and more especially to the production of metabolites by plant cells. The term "metabolites" is to be understood to mean de novo biosynthetic, biotransformation or biodegradation products produced by plant cells.

It is known that plant cells cultivated in vitro can, in some cases, biosynthesise or transform metabolites of economic value (M. H. ZENK: The impact of plant cell culture on industry, in T. A. THORPE (editor): The International Association for plant tissue culture - Calgary 1978 (pages 1-14)).

The industrial utilisation of this potential is currently limited because of the cost of the plant cell cultures when they are carried out in the traditional bioreactors. This cost, which is much higher than that in processes using microorganisms, is mainly due to the long cultivation time, which is itself caused by the slow proliferation of the cells.

By way of example, the maximum growth rates and the generation times of various microorganisms and of plant cells are reported in the table below:

|  | bacterium | yeast | filamentous fungus | plant cell |
|---|---|---|---|---|
| generation time tg in hours | 0.3 | 1.5 | 3 | 24 |
| maximum growth rate $\mu_m$ (hour$^{-1}$) | 2.3 | 0.46 | 0.23 | 0.0287 |

The maximum growth rate is represented by the ratio:

$$\frac{dX}{dT} / X$$

$X$ = biomass
$T$ = time

While this comparison has little meaning from the biological point of view because it does not take account of the size of the organisms, from an operational point of view, it is clear that the plant cell is the least favoured organism for carrying out biotechnological processes, at least in cases where the desired production is directly dependent on the production of biomass.

Processes involving the utilisation of the nutrient medium have therefore been studied and it has been clearly shown (V. PETIARD, 1980, Physiologie Végétale 18,2,331-337) that some tissue strains can diffuse the metabolites which they have biosynthesised into the nutrient medium. One of these processes consists in the realisation of bio reactors with cells which are immobilised either by inclusion in alginate gels (A. W. ALFERMANN, I. SCHULLER and E. REINHARD, Planta Medica, 1980, page 281; P. BRODELIUS, B. DEUS, K. MOSBACH and M. H. ZENK, Febs. Letters, 103, 1, 93-97) or by fixing to various carriers.

The present invention provides a process which involves the same general type of reactor, but which is carried out in the absence of any means for immobilising the plant cells.

The process of the present invention for the cultivation of plant cells comprises cultivating the said cells in a liquid medium without agitating or fixing the cells, the liquid medium being continuously or intermittently removed and replaced.

The process may, for example, be operated as follows:

The plant cells are placed, in the form of cell aggregates of variable size (ranging from an isolated cell to a callus), in a non-agitated liquid medium contained in a reactor. The medium is circulated to ensure the nutrition, the oxygenation and, if appropriate, the extraction of the excreted metabolites. The biomass remains settled in the reactor by virtue of an appropriate filter, e.g. of glass filter, stainless steel gauze, nylon cloth or the like as in the reactor of fixed cells. The size of the aggregates makes it possible to minimise clogging phenomena, compared with the clogging that would be expected with microorganisms.

BRIEF DESCRIPTION OF THE DRAWINGS

FIG. 1 of the accompanying drawings shows one model of the equipment. Any other model which permits the cultivation of plant cells in a non-agitated liquid medium and in the absence of any means for the fixing or inclusion of the cells can be used to carry out the invention.

The process of the present invention can be applied to plant cells of all so-called higher or phanerogamous plant species.

The applications of the process of the present invention can be as diverse as those of processes for the cultivation of plant cells in suspension in conventional reactors. They include the production of any component of the primary or secondary metabolism of the plant cell, for example, enzymes, essential oils, flavourings, steroids, pigments, alkaloids, flavones, heterosides, and new compounds exhibiting valuable pharmacological or cosmetological activities.

These applications also include the specific biotransformation of particular substrates to specific compounds desired for various reasons, or the biodegradation of particular substances.

The process of the present invention can thus be applied in various industrial fields, e.g. in the field of foodstuffs, pharmaceuticals, pure chemistry and cosmetics.

It is possible to cultivate plant tissues in the form of settled calluses in a liquid medium, that is to say under oxygenation conditions which are limited to surface exchanges and are consequently extremely restricted.

The following Examples illustre the invention. In general, outside the process of the invention, conventional techniques of those skilled in the art are used (for sterilisation of the media, cultivation conditions, extraction and the like). Example 1 describes the adaptation of a plant cell culture to growth in a liquid medium without agitation nor circulation of the medium. In this example no isolation of any product is described.

EXAMPLE 1: Preparation and multiplication of immersed calluses of *Vinca minor* L.

One of our strains of *Vinca minor* L tissues, of reference Vml, is in the form of calluses cultivated on a semi-solid agar treated medium of the following composition:

| Component | Concentration in mg/liter of medium |
|---|---|
| (a) so called Heller solution of inorganic macro-constituents | |
| potassium chloride | 750 |
| sodium nitrate | 600 |
| magnesium sulphate heptahydrate | 250 |
| monosodium phosphate monohydrate | 125 |
| calcium chloride dihydrate | 75 |
| (b) so called Heller solution of inorganic oligo-constituents | |
| zinc sulphate heptahydrate | 1 |
| boric acid | 1 |
| manganese sulphate tetrahydrate | 0.1 |
| copper sulphate pentahydrate | 0.03 |
| aluminium chloride hexahydrate | 0.05 |
| potassium iodide | 0.01 |
| nickel chloride hexahydrate | 0.03 |
| (c) source of iron | 1 mg/liter of medium |
| ferric chloride hexahydrate | |
| (d) solution of vitamins, reference B1 | |
| calcium pantothenate | 1 |
| pyridoxine | 1 |
| nicotinic acid | 1 |
| thiamine | 1 |
| meso-inositol | 10 |
| biotin | 0.01 |
| (e) growth substances | |
| 2-(2,4-dichlorophenoxy)-acetic acid | 1 mg/liter of medium |
| 6-(furfurylamino)-purine (kinetin) | 1 mg/liter of medium |
| (f) carbon substrate: sucrose | 20 g/liter of medium |
| (g) solidifying agent: agar | 7 g/liter of medium |

The cultures are carried out in test tubes and placed under homogeneous conditions at a temperature of 23° C. and under the following lighting conditions:
luminous spectrum of the type from a Sylvania Grolux lamp
luminous intensity about 5,000 lux
period of illumination: 16 hours/day
culture cycle: (between two subcultures): 4 weeks Under these conditions, the calluses are relatively chlorophyllaceous and very hard and they have a growth rate of 225%, expressed according to the formula:

$$\frac{WfH - Wfl}{Wfl} \times 100$$

i.e. $\frac{\text{Weight of fresh material harvested} - \text{Weight of fresh material in the implant}}{\text{Weight of fresh material in the implant}} \times 100$ Their solids content is 7.11% $\left(\frac{\text{dry material}}{\text{fresh material}} \times 100\right)$ When sub-culturing this strain a few calluses were placed under strictly the same conditions, whereas other calluses were placed in an identical medium except for the agar, which was omitted. It is therefore a liquid medium (10 ml/test tube).

About twelve hours after the inoculation, the calluses are settled at the bottom of the test tube and covered by about 2.5 to 3 cm of liquid medium.

After several sub-cultures, under these conditions, of the calluses which have shown the best growth, a strain is obtained which has a substantially identical appearance to that of the strain cultivated under the initial conditions.

The growth rate of this strain for the same cultivation time is 313%. It is therefore greater than that of the initial strain on agar medium. The dry content of the tissues obtained under these conditions is 5.99%. Therefore it is possible to cultivate plant calluses in a liquid medium without agitation nor circulation of the medium and without fixation of the cells.

EXAMPLE 2

Column cultivation of a strain of *Catharanthus roseus* G. Don, of reference CR2 - Batch production One of our strains, of reference CR2, of *Catharanthus roseus* tissues has a low capacity for the biosynthesis and excretion of metabolites, but it was singled out for its antimitotic activity (V. PETIARD, 1980, "International Research Congress on Natural Products as Medicinal Agents").

It is conventionally cultivated in Petri dishes on a semi-solid medium having the following composition:

| Components | Concentration in mg/liter of medium |
|---|---|
| (a) so-called Murashige and Skoog solution of macro-constituents | |
| ammonium nitrate | 1,650 |
| potassium nitrate | 1,900 |
| calcium chloride hydrate | 440 |
| magnesium sulphate heptahydrate | 370 |
| potassium phosphate | 170 |
| (b) so called Heller solution of oligo-constituents (see Example 1) | |
| (c) solution of vitamins, of reference B1 (see Example 1) | |
| (d) ferric chloride hexahydrate | 1 mg/liter |
| (e) growth substances | |
| naphthyl-1-acetic acid | 1 mg/liter |
| 6-(furfurylamino)-purine | 1 mg/liter |
| (f) carbon substrate: glucose | 30 g/liter |
| (g) solidifying agent: agar | 7 g/liter |

The strain is maintained by regular sub-cultivation every 4 weeks.

Four-week-old calluses of this strain are placed under sterile conditions in equipment, such as that of FIG. 1, containing a nutrient medium of identical composition except for the agar, which has been omitted therefrom. This equipment comprises: a cultivation column 1 (capacity 3 liters) comprising, in its lower part, a means for separating the tissues from the liquid medium, which consists of a sintered glass filter 2 to prevent entraining of tissues. A glass tube 3, placed at the top of the column, enables the nutrient medium to enter; another glass tube 4, placed below the sintered glass plate, enables the same medium to leave after it has circulated over the tissues and without risk of entraining these tissues; a glass carboy 5 (of capacity 5 liters) which can be thermostated and can receive various means for aerating the nutrient medium or for measuring some of its characteristics (temperature, pH, density of dissolved oxygen tension. A means of agitation 6 can also be introduced into the carboy to ensure a better oxygen transfer;

a glass tube 7, placed in its upper part, enables the nutrient medium to return after it has passed through the cultivation column. Another glass tube 8, placed in its lower part, enables the medium to leave towards the cultivation column; the way of circulation may be reversed, if necessary.

a means for equilabrating the pressure between the two main components of this equipment can also be attached;

a pump 9 which enables the medium to be circulated between these two containers. In the present Example, the pump is placed in the circuit in which the medium returns towards the carboy 5.

The circulation rate between the column 1 and the carboy 5 is 56 ml/minute. The temperature of the medium is kept at 30° C. and controlled in the region of the lower part of the column. The tissues remained at substantially the same chlorophyll level throughout the cultivation period. After 4 months under these conditions, the biomass and medium together were harvested. The weight of fresh biomass material increased by about 100% (in 4 months), which represents a relatively slow growth compared with the same strain cultivated on agar medium (1,000% in 4 weeks).

The amount of crude alkaloid extract obtained by this process is about 95 mg, namely 50 mg from the biomass and 45 mg from the liquid medium (5.6 mg/liter×8 liters). This amount of alkaloid extract was thus obtained in 4 months from an inoculum equivalent to the biomass harvested from 10 Petri dishes. In cultivation on agar medium, this same biomass produces 15 mg/month (12 mg in the tissues and 3 mg in the agar medium), that is to say 15×4=60 mg over a period of 4 months. Overall, the production of crude alkaloid extract by the present process is approximately 1.5 times greater than that obtained under the reference conditions.

It should be noted that the tissue/medium distribution is different in the two cases and is more favourable with respect to the medium in the process of the invention.

Qualitatively, the composition of this extract is substantially identical to that of extracts obtained conventionally. Certain alkaloid compounds easily detectable by two-dimensional thin layer chromatography, such as ajmalicine, serpentine, (−) tabersonine and the like, are present therein.

EXAMPLE 3

Column cultivation of a strain of *Catharanthus roseus G. Don,* of reference CR2 - Semi-continuous or continuous production.

The same strain as that described in Example 2 was cultivated in the same type of equipment, to which a means for the semi-continuous or continuous removal of the nutrient medium was attached in the region of the carboy 5.

Table 1 below indicates the amounts of crude alkaloid extract obtained from the nutrient medium when it was totally replaced after different periods of circulation through the tissue column.

TABLE 1

| Frequency of renewal | Concentration of CE in the medium | Total CE obtained in the medium (for 8 liters) | Production of CE per week | Production of CE per 4 weeks | Production ratio LM/SM (medium)/ (tissues + medium) | Production ratio LM/SM (medium alone) |
|---|---|---|---|---|---|---|
| 1 week | 2.95 mg/liter | 24 mg | 24 mg | 96 mg | 96/15 ≈ 6.5 | 96/3 = 32 |
| 2 weeks | 3.10 mg/liter | 24.8 mg | 12.4 mg | 49.6 mg | 49.6/15 ≈ 3.3 | 49.6/3 ≈ 16.5 |
| 3 weeks | 3.20 mg/liter | 25.6 mg | 8.5 mg | 34 mg | 34/15 ≈ 2.3 | 34/3 ≈ 11 |
| 4 weeks | 3.80 mg/liter | 30.4 mg | 7.5 mg | 30 mg | 30/15 = 2 | 30/3 = 10 |

LM = liquid medium (in a column)
CE = crude extract
SM = solid medium (in Petri dishes)
PRODUCTION IN A SOLID MEDIUM FOR THE SAME AMOUNT OF BIOMASS HARVESTED AFTER 4 WEEKS OF CULTIVATION: 15 mg. (12 mg being in the tissues and 3 mg in the medium).

A comparison with the production from cultivation on agar medium is made for an equivalent amount of tissues, that is to say for the amount harvested from 10 Petri dishes after 4 weeks of cultivation. Under the latter conditions, 15 mg of extracts are obtained, distributed as 12 mg in the tissues and 3 mg in the agar medium.

This table clearly shows that:

the concentration in the medium is identical, regardless of the frequency of replacing the nutrient medium (from 1 to 4 weeks in the present example), and the coefficient of improvement in the yield per unit time and per unit of biomass, relative to cultivation on a solid medium, is the higher, the lower is the time between two replacings of the liquid medium.

It must be noted that, for the process described, this comparison only takes into account the extract obtained from the liquid medium. The value of process is even more pronounced if this production is compared not with the extract of the tissues+medium together, from the cultures on a solid medium, but with the extract of the agar-treated medium alone.

For this strain, the presence of alkaloids in the medium thus seems due to a diffusion equilibrium. Under these conditions, the total replacing of the nutrient medium makes it possible to bring its concentration of crude alkaloid extract to 0 and consequently to enhance the phenomenon of diffusion of the alkaloids from the biomass towards the medium and to induce more higher biosynthetical activity.

The increase in the volume of medium in circulation over the same amount of biomass, or the permanent displacement of the tissue/medium equilibrium concentration, are means which make it possible to utilise this diffusion phenomenon even better.

Example 4 describes one of these processes.

EXAMPLE 4

Column cultivation of a strain of *Catharanthus roseus* G. Don, of reference $CR_2$ - Semi-continuous or continuous extraction of the metabolites excreted into the medium The same strain as that described in Examples 2 and 3 was cultivated in the same type of equipment, to which a means for the continuous extraction of the alkaloids contained in the medium was attached.

This means consists of an extraction column filled either with a water-immiscible organic solvent (chloroform, methylene chloride or the like) or with resins specifically permitting the fixing of alkaloids (for example Amberlite $XAD_2$). This extraction column can be placed either directly in the circuit for circulation of the medium or in parallel with the carboy 5. It can thus be used either continuously or sporadically (for example once per day). Using this process, and for the same reasons as those stated in Example 3, the production level in the liquid medium per unit time and per unit of biomass is greatly increased. It is increased by a factor of 10 or 50, depending on whether or not the comparison takes into account the extract of the tissues harvested on agar medium. In contrast to the process described in Example 3, this increase is achieved without renewal of the nutrient medium and hence without unnecessary loss of the products of which it is composed. This is more particularly important for the carbon substrate, for which the demand is relatively low, taking account of the low growth rates of the biomass cultivated under these conditions.

EXAMPLE 5

Column cultivation of a strain of *Catharanthus roseus* G. Don, of reference $CR_{20}$ - Batch, semi-continuous or continuous production or production with continuous extraction Another of our strains of *Catharanthus roseus*, of reference $CR_{20}$, is cultivated in suspension in an agitated liquid medium. The composition of this nutrient medium is as follows:

| Components | Concentration in mg/liter of medium |
| --- | --- |
| (a) solution of inorganic macro-constituents, so called B5 of Gamborg | |
| potassium nitrate | 2,500 |
| ammonium sulphate | 134 |
| monosodium phosphate monohydrate | 150 |
| magnesium sulphate heptahydrate | 250 |
| calcium chloride dihydrate | 150 |
| (b) solution of inorganic oligo-constituents, so called B5 of Gamborg | |
| manganese sulphate monohydrate | 10 |
| boric acid | 3 |
| zinc sulphate heptahydrate | 2 |
| sodium molybdate dihydrate | 0.250 |
| copper sulphate pentahydrate | 0.0250 |
| cobalt chloride hexahydrate | 0.0250 |
| potassium iodide | 0.750 |
| (c) solution of vitamins | |
| meso-inositol | 100 |
| nicotinic acid | 1 |
| thiamine | 10 |
| pyridoxine | 1 |
| (d) source of iron | |
| ethylenediaminetetraacetic acid dihydrate | 37.3 mg/liter |
| ferrous sulphate heptahydrate | 27.8 mg/liter |

-continued

| Components | Concentration in mg/liter of medium |
| --- | --- |
| (e) growth substances | |
| 2-(2,4-dichlorophenoxy)-acetic acid | 1 mg/liter of medium |
| 6-(furfurylamino)-purine (kinetin) | 0.06 mg/liter of medium |
| (f) carbon substrate: sucrose | 20 g/liter of medium |

This strain $CR_{20}$ is cultivated in suspension in Erlenmeyer flasks stirred at a speed of 100–120 rpm and at a temperature of 26° C. It is maintained by regular subculture every 14 days in new nutrient medium. Under these conditions, it reaches a maximum density of $1.5 \times 10^6$ cells/ml. It is in the form of very fine cell aggregates which permit sub-culture by simply removing an aliquot.

In the present Example, this strain is cultivated in two successive stages:

in a first stage, it is cultivated at 30° C. in a conventional bioreactor with a useful capacity of 4.5 liters, in an agitated and aerated liquid medium. Under these conditions, it reaches a density maximum of about 250 g of fresh material per liter of culture. This is therefore a first stage of multiplication of the biomass; and in a second stage, the biomass thus obtained is placed in equipment identical to that described in Example 2 and shown in FIG. 1.

Very rapidly, the whole of the biomass settles on the sintered glass plate of the column 1. The cultivation temperature is kept at 30° C. at the bottom of the column and the circulation rate of the medium is also 56 ml/minute. An aeration of 0.1 V.V.M. (volume/-volume/mm) is maintained in the carboy 5. The tissues retain a yellowish-white colouration and no browning phenomenon characteristic of necrosis appears throughout the culture period.

After 4 months of cultivation under these conditions, the tissues and medium together are harvested. The growth rate is about 100%. There has therefore been a slow growth, which had moreover been observed by an increase in the level of the biomass in the column 1. The amount of crude alkaloid extract obtained under these conditions, for an equivalent amount of tissues, is about 2 times greater than that which was obtained from cultures in an agitated liquid medium (in an Erlenmeyer flask or a reactor) during the same period. Qualitatively, these extracts are completely similar to those originating from cultures prepared conventionally. Amongst other compounds, the presence of ajmalicine and serpentine can be observed in these extracts.

The various improvements in the process, described in Examples 3 and 4 for the strain $CR_2$, were also put into effect for the strain $C_{20}$. They increased the yield per unit time by a factor of about 5.

Thus, plant cell cultures in a non-agitated liquid medium can also be prepared from cell suspensions developed in conventional bioreactors.

EXAMPLE 6

Column cultivation of a strain of *Papaver somniferum*, of reference PS 167

One of our strains of *Papaver somniferum*, of reference PS 167, is cultivated in test tubes on a semi-solid medium having the following composition:

(a) so-called Heller solution of inorganic macroconstituents (see Example 1)
(b) so-called Heller solution of inorganic oligoconstituents (see Example 1)
(c) ferric chloride hexahydrate 1 mg/liter of medium
(d) solution of vitamins, of reference $B_1$ (see Example 1)

| (e) grow substances | |
| --- | --- |
| 2-(2,4-dichlorophenoxy)-acetic acid | 0.1 mg/liter of medium |
| 6-(furfurylamino)-purine (kinetin) | 1 mg/liter of medium |
| (f) carbon substrate: glucose | 30 g/liter of medium |
| (g) solidifying agent: agar | 7 g/liter of medium |

The cultures are placed under the same conditions as those described for the strain of *Vinca minor* in Example 1.

The calluses are friable and relatively chlorophyllaceous. This strain was selected for its capacity to biosynthesise some poppy alkaloids without any morphogenic differentiation.

Equipment such as described in Example 2, containing a liquid medium of identical composition to that indicated above, except that the agar has been omitted therefrom, is inoculated with 5-week-old cultures of this type. Morphologically, the culture retains its appearance and does not show necrosis phenomena. The circulation rate of the medium through the column 1 is 56 ml/minute. After 3 months of cultivation under these conditions, the biomass and the medium are harvested and extracted in a conventional manner. The weight of fresh material harvested has increased by 200%, relative to that of the implant.

In the same way as in the previous Examples, the yield of crude alkaloid extract of the biomass and of the medium is slightly greater than that observed for the cultures under conventional conditions, that is to say on agar medium in test tubes.

Also in this Example, the increase in yield is mainly due to the presence, in the liquid medium circulating over the tissues, of more than 50% of the extract produced. Putting into effect the improvements in the process, described in Examples 3 and 4 (replacing of the medium, continuous extraction), enhances the value of the present invention.

EXAMPLE 7

Column cultivation of a strain of *Medicago sativa*, of reference Ms $CK_2$

One of our strains of *Medicago sativa*, of reference Ms $CK_2$, is cultivated in the form of a cell suspension in an agitated Erlenmeyer flask.

It is cultivated at 27° C. in the dark and has the characteristic of using lactose as the only source of carbon substrate. It was possible to show, in the course of fermentor studies, that this possibility of using lactose was due to two $\beta$-galactosidase activities, one being localised in the cells and one being localised on the wall and in the nutrient medium.

The nutrient medium for this strain has the following composition:

(a) so-called Murashige and Skoog solution of inorganic micro-constituents (see Example 2)
(b) so-called Heller solution of inorganic microconstituents (see Example 1)
(c) source of iron: see Example 5
(d) solution of vitamins, of reference $B_1$ (see Example 1)
(e) growth substance

| | |
| --- | --- |
| naphthyl-1-acetic acid | 1 mg/liter of medium |
| 6-(furfurylamine)-purine | 1 mg/liter of medium |
| (f) carbon substrate: lactose | 30 g/liter of medium |

In the present Example, this strain is cultivated in 2 successive stages:

in a first stage, it is cultivated at 27° C. in a fermentor with a useful capacity of 3.5 liters, with a blade stirrer rotating at 80 rpm (rotations per minute). The dissolved oxygen tension in the medium is kept above 1.5 ppm. For this purpose, the aeration level is modified from 0.03 V.V.M. to 0.5 V.V.M. Under these conditions, the culture reaches a density of 300 g of fresh material per liter in 250 hours:

in a second stage, the biomass thus obtained is transferred into the column 1 of the equipment described in Example 2, containing the same nutrient medium.

Under these conditions, the tissues settle rapidly. The temperatures is kept at 27° C. and controlled at the bottom of the column 1 and the circulation rate of the medium is fixed at 100 ml/minute. An aeration of 0.25 V.V.M. is maintained in the carboy 5.

The morphological appearance of the culture remains identical for more than 3 months. It was also possible to show that, under these conditions, the culture retained its capacity to hydrolyse lactose (drop in the concentration of lactose in the medium and increase in the concentrations of glucose and galactose), and that the nutrient medium had a $\beta$-galactosidase activity (O.N.P.G. activity).

This Example shows that the process of the present invention is also an effective means for the enzymatic transformation of certain substrates.

It is clearly apparent from these Examples that the process of the present invention makes it possible to cultivate plant cells in vitro, for long periods, without agitation and in the absence of any artificial carrier for the inclusion or fixing of these cells, and to utilise certain potentialities of their metabolism under these conditions.

The process of the present invention makes it possible:

to keep cultures in the stage of producing certain metabolites for very long periods of more than 4 to 6 months;

greatly to facilitate the production when, under the conventional conditions, it is totally out of phase with the growth, because it makes it possible easily to arrest or inhibit the growth;

to utilise to best advantage the phenomena of diffusion towards the nutrient medium, and thus greatly to increase the production per unit of biomass and per unit of time; therefore to increase the productivity of the bioreactor to carry out continuous extraction of the biosynthesised products and thus to improve the production efficiency, relative to the nutrient substrate used; and to use strains which prove impossible or difficult to adapt to cultivation in an agitated liquid medium, or the production capacity of which is only expressed with some morphological differentiations existing only at the level of the calluses and not at the level of the suspension cultures.

By virtue of its simplicity, the process of the present invention also has numerous other advantages over the conventional processes of cultivation in an agitated liquid medium; it limits the risks of contamination, the costs of use (energy, amount of medium consumed) and the costs of absorption of depreciation (simplicity of the equipment).

For these various reasons, the process of the present invention is capable of being used in numerous applications for the production or the biotransformation of natural substances of plant origin, in a manner which is competitive with the extraction of the whole plant or organic synthesis.

We claim:

1. A process for the in vitro cultivation of plant cells in a liquid nutrient medium which comprises:
   (a) providing an essentially vertical cultivator column fitted with a filter near its bottom pervious to the nutrient medium but not to the plant cells;
   (b) placing the plant cells to be cultivated and a nutrient medium therefor in the cultivator column and permitting the cells to settle to the lower portion of the column and form a biomass, the cells not being immobilized;
   (c) removing a portion of the nutrient medium from the cultivator column at a point below the filter and passing the portion removed to a reservoir containing additional nutrient medium; and
   (d) replenishing the nutrient medium in the cultivator column with nutrient medium from the reservoir, said replenishing medium being introduced into an upper portion of the cultivator column above the biomass and without agitating the biomass.

2. A process according to claim 1 in which removal of liquid nutrient medium from the cultivator column is intermittent.

3. A process according to claim 1 in which removal of liquid nutrient medium from the cultivator column is continuous.

4. A process according to claim 3 in which metabolites produced by the plant cells being cultivated are continuously removed from the liquid nutrient medium present in the reservoir.

5. A process according to claim 1 in which the plant cells being cultivated are callus cells.

6. A process according to claim 1 in which the plant cells being cultivated are obtained from a cell suspension produced in a fermentor.

7. A process according to claim 1 in which the plant cells being cultivated are from a phanerogam.

8. A process according to claim 1 in which an increase in the weight of the cells is partially or totally limited by omitting a constituent of the liquid nutrient medium.

* * * * *